(12) United States Patent
Ma et al.

(10) Patent No.: US 12,226,210 B2
(45) Date of Patent: Feb. 18, 2025

(54) BLOOD COLLECTION DEVICE AND RELATED SYSTEMS AND METHODS

(71) Applicant: Becton, Dickinson and Company, Franklin Lakes, NJ (US)

(72) Inventors: Yiping Ma, Layton, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 410 days.

(21) Appl. No.: 17/401,506

(22) Filed: Aug. 13, 2021

(65) Prior Publication Data
US 2022/0047195 A1 Feb. 17, 2022

Related U.S. Application Data

(60) Provisional application No. 63/065,785, filed on Aug. 14, 2020.

(51) Int. Cl.
*A61B 5/00* (2006.01)
*A61B 5/15* (2006.01)
(Continued)

(52) U.S. Cl.
CPC .. *A61B 5/150992* (2013.01); *A61B 5/150267* (2013.01); *A61M 25/0082* (2013.01); *A61M 39/12* (2013.01); *A61M 2039/1077* (2013.01)

(58) Field of Classification Search
CPC ........ A61B 5/150992; A61B 5/150267; A61B 5/150946; A61B 5/150389;
(Continued)

(56) References Cited

U.S. PATENT DOCUMENTS 5,147,329 A * 9/1992 Brannon .......... A61B 5/150236
604/231
5,697,914 A * 12/1997 Brimhall .......... A61M 25/0631
604/177
(Continued)

FOREIGN PATENT DOCUMENTS

| WO | 9929232 A1 | 6/1999 |
| WO | 2014172232 A1 | 10/2014 |
| WO | 2020146178 A1 | 7/2020 |

*Primary Examiner* — May A Abouelela
(74) *Attorney, Agent, or Firm* — The Webb Law Firm (57) ABSTRACT

A blood collection device to reduce hemolysis in a peripheral intravenous catheter system may include a distal end. The distal end of the blood collection device may include a male luer adapter, which may include a distal opening. The blood collection device may include a cannula in fluid communication with the male luer adapter. The cannula may include a distal end and a sharp proximal tip. The blood collection device may include an elongated neck disposed between the male luer adapter and the sharp proximal tip. The blood collection device may include a fluid pathway extending from the distal opening through the sharp proximal tip. A diameter of the fluid pathway may be constant. An entire length of the fluid pathway is represented by L, and the diameter of the fluid pathway is represented by D. $D^4/L$ may be equal to or less than a predetermined value.

16 Claims, 6 Drawing Sheets

(51) Int. Cl.
*A61M 25/00* (2006.01)
*A61M 39/12* (2006.01)
*A61M 39/10* (2006.01)

(58) Field of Classification Search
CPC ........ A61B 5/150519; A61B 5/150572; A61B 5/154; A61B 5/15003; A61M 25/0082; A61M 39/12; A61M 2039/1077; A61M 39/10; A61M 25/0097; A61M 2039/1038; A61M 25/0021; A61M 25/0043; A61M 2210/12

See application file for complete search history.

(56) References Cited

U.S. PATENT DOCUMENTS

| | | | | |
|---|---|---|---|---|
| 5,984,895 | A * | 11/1999 | Padilla | A61M 25/0693 604/168.01 |
| 6,595,954 | B1 * | 7/2003 | Luther | A61M 25/0618 604/110 |
| 6,616,637 | B2 * | 9/2003 | Alexander | A61B 5/15003 604/192 |
| 7,530,967 | B2 * | 5/2009 | Brown | A61B 5/150389 604/122 |
| 8,383,044 | B2 * | 2/2013 | Davis | A61B 5/150267 600/580 |
| 9,028,425 | B2 * | 5/2015 | Burkholz | A61B 5/15074 600/577 |
| 10,080,516 | B2 * | 9/2018 | Ellis | A61B 5/15101 |
| 10,238,325 | B2 * | 3/2019 | Burkholz | A61B 5/150412 |
| 10,791,975 | B2 * | 10/2020 | Wilkinson | A61B 5/150778 |
| 11,097,083 | B2 * | 8/2021 | Burkholz | A61M 39/162 |
| 11,419,531 | B2 * | 8/2022 | Bullington | A61B 5/15003 |
| 2003/0055381 | A1 * | 3/2003 | Wilkinson | A61B 5/150641 604/177 |
| 2003/0105414 | A1 * | 6/2003 | Leong | A61B 5/15003 600/576 |
| 2004/0143226 | A1 * | 7/2004 | Marsden | A61B 5/150671 604/272 |
| 2009/0204026 | A1 * | 8/2009 | Crawford | A61B 5/150671 600/576 |
| 2009/0259201 | A1 * | 10/2009 | Hwang | A61B 5/150648 604/263 |
| 2011/0178427 | A1 * | 7/2011 | Tan | A61B 5/154 600/576 |
| 2014/0309551 | A1 * | 10/2014 | Burkholz | G01N 33/491 600/573 |
| 2014/0364766 | A1 * | 12/2014 | Devgon | A61B 5/150221 600/581 |
| 2016/0073937 | A1 | 3/2016 | Burkholz et al. | |
| 2016/0081606 | A1 * | 3/2016 | Russ | A61B 5/150503 600/578 |
| 2018/0140240 | A1 | 5/2018 | Bullington et al. | |
| 2019/0022357 | A1 * | 1/2019 | Burkholz | A61M 25/0032 |
| 2019/0175088 | A1 * | 6/2019 | Burkholz | A61M 1/34 |
| 2019/0321599 | A1 * | 10/2019 | Burkholz | A61M 39/10 |
| 2020/0046948 | A1 * | 2/2020 | Burkholz | A61B 5/154 |
| 2020/0170559 | A1 * | 6/2020 | Burkholz | A61M 5/3137 |
| 2020/0391012 | A1 * | 12/2020 | Thirumoorthy | A61M 25/0631 |

* cited by examiner

BLOOD COLLECTION DEVICE AND RELATED SYSTEMS AND METHODS

CROSS-REFERENCE TO RELATED APPLICATION

The present application claims priority to U.S. Provisional Application Ser. No. 63/065,785, entitled "Blood Collection Device and Related Systems and Methods" filed Aug. 14, 2020, the entire disclosure of which is hereby incorporated by reference.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may remove the needle, leaving the catheter in place for future blood withdrawal or fluid infusion.

For blood withdrawal or collecting a blood sample from a patient, a blood collection container may be used. The blood collection container may include a syringe or a test tube with a rubber stopper at one end. In some instances, the blood collection container has had all or a portion of air removed from the test tube so pressure within the blood collection container is lower than ambient pressure. Such a blood collection container is often referred to as an internal vacuum or a vacuum tube. A commonly used blood collection container is a BD VACUTAINER® tube, available from Becton Dickinson & Company of Franklin Lakes, New Jerse.

The blood collection container may be coupled to the catheter. When the blood collection container is coupled to the catheter, a pressure in the vein is higher than a pressure in the blood collection container, which pushes blood into the blood collection container, thus filling the blood collection container with blood. A vacuum within the blood collection container decreases as the blood collection container fills, until the pressure in the blood collection container equalizes with the pressure in the vein, and the flow of blood stops.

Unfortunately, as blood is drawn into the blood collection container, red blood cells are in a high shear stress state and susceptible to hemolysis due to a high initial pressure differential between the vein and the blood collection container. Hemolysis may result in rejection and discard of a blood sample. The high initial pressure differential can also result in catheter tip collapse, vein collapse, or other complications that prevent or restrict blood from filling the blood collection container.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to blood collection devices and related systems and methods. In some embodiments, a peripheral intravenous catheter system may reduce a risk of mechanical hemolysis during blood collection from a vasculature of a patient. In some embodiments, the peripheral intravenous catheter system may include a peripheral intravenous catheter, and a female luer adapter coupled to the peripheral intravenous catheter.

In some embodiments, the peripheral intravenous catheter system may include a blood collection device, which may include a distal end. In some embodiments, the distal end of the blood collection device may include a male luer adapter, which may be coupled to the female luer adapter. In some embodiments, the male luer adapter may include a distal opening. In some embodiments, the blood collection device may include a cannula in fluid communication with the male luer adapter. In some embodiments, the cannula may include a distal end and a sharp proximal tip. In some embodiments, the blood collection device may include an elongated neck disposed between the male luer adapter and the sharp proximal tip. In some embodiments, the blood collection device may include a fluid pathway extending from the distal opening through the sharp proximal tip.

In some embodiments, the peripheral intravenous catheter is 22 G-18 G (inclusive), and an entire length of the fluid pathway is 2 inches. In some embodiments, the peripheral intravenous catheter is 24 G, and the entire length of the fluid pathway is 5.4 inches. In some embodiments, the entire length of the fluid pathway is between 2 inches and 5.4 inches, inclusive.

In some embodiments, a diameter of the fluid pathway is constant, the entire length of the fluid pathway is represented by L, and the diameter of the fluid pathway is represented by D. In some embodiments, the diameter of the fluid pathway may be greater than a minimum inner diameter of the peripheral intravenous catheter. In some embodiments, $D^4/L$ is equal to or less than a predetermined value, which may be based on a gauge of the peripheral intravenous catheter.

In some embodiments, the gauge of the peripheral intravenous catheter is 24 G, and $D^4/L$ is equal to or less than 5.8E-08 cubic inches. In some embodiments, the gauge of the peripheral intravenous catheter is 22 G, and $D^4/L$ is equal to or less than 1.6E-07 cubic inches. In some embodiments, the gauge of the peripheral intravenous catheter is 20 G, and $D^4/L$ is equal to or less than 3.1E-07 cubic inches. In some embodiments, the gauge of the peripheral intravenous catheter is 18 G, and $D^4/L$ is equal to or less than 5.8E-08 cubic inches.

In some embodiments, the male luer adapter of the blood collection device may include a collar. In some embodiments, an outer diameter of the collar may be greater than an outer diameter of the elongated neck. In some embodiments, the blood collection device may include a holder configured to receive a blood collection tube. In some embodiments, the holder may include a cylindrical body. In some embodiments, the sharp proximal tip is disposed in a center of the cylindrical body. In some embodiments, an outer diameter of the holder may be greater than the outer diameter of the elongated neck. In some embodiments, the elongated neck may be disposed between the holder and the collar. In some embodiments, the distal end of the cannula may be integrated within the elongated neck. In some embodiments, the blood collection device may be gauge specific or configured for use with a specific gauge of the catheter. In some embodiments, the blood collection device may be configured for use with a single gauge of the catheter or with more than one gauge of the catheter. In some embodiments, D may be greater than or equal to an inner diameter of the catheter.

In some embodiments, the blood collection device may include another female luer adapter disposed at a proximal end of the elongated neck. In some embodiments, the distal end of the holder may include another male luer adapter. In some embodiments, the other female luer adapter may be coupled to the other male luer adapter.

It is to be understood that the foregoing general description and the following detailed description are examples and explanatory and are not restrictive of the present disclosure. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
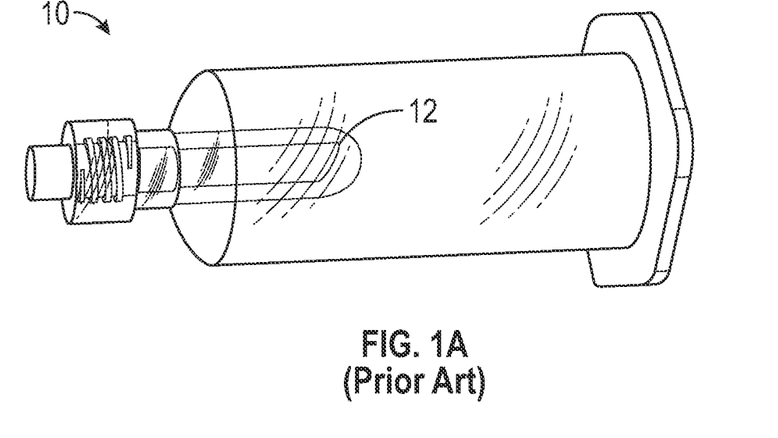
FIG. 1A is an upper perspective view of a prior art blood collection device.
Figure 1B:
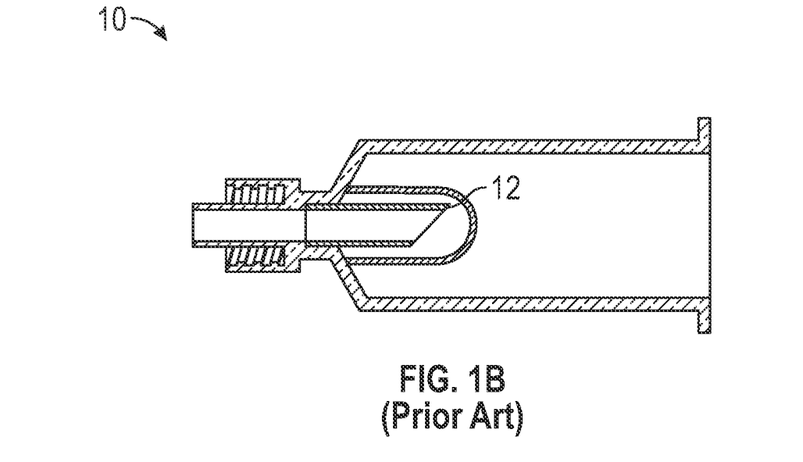
FIG. 1B is a cross-sectional view of the prior art blood collection device.

Referring now to FIGS. 1A-1B, a prior art blood collection device 10 is illustrated. The prior art blood collection device 10 may correspond to a BD VACUTAINER® LUER-LOK™ access device, available from Becton Dickinson & Company of Franklin Lakes, New Jersey. The prior art blood collection device 10 is typically used during blood draw via an extension set of a catheter assembly inserted into vasculature of a patient. The prior art blood collection device 10 is configured to receive a blood collection container, such as a BD VACUTAINER® tube. The prior art blood collection device 10 includes a cannula 12 that is configured to punctuate a rubber stopper of the BD VACUTAINER® tube in response to the BD VACUTAINER® tube being inserted into the prior art blood collection device 10.

Figure 2A:
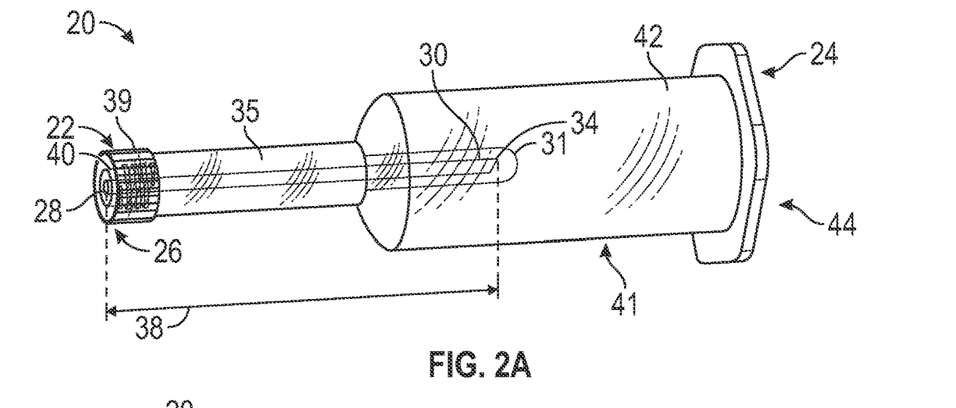
FIG. 2A is an upper perspective view of an example blood collection device, according to some embodiments.
Figure 2B:
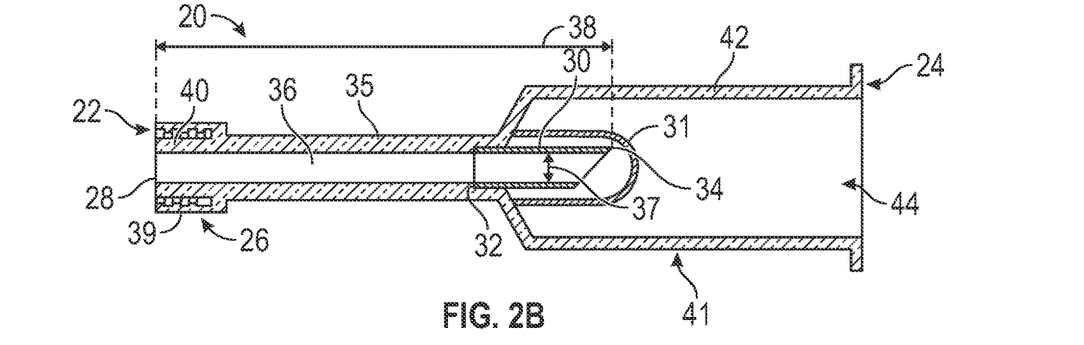
FIG. 2B is a cross-sectional view of the blood collection device, according to some embodiments.

Referring now to FIGS. 2A-2B, a blood collection device 20 is illustrated, according to some embodiments. In some embodiments, the blood collection device 20 may include a distal end 22 and a proximal end 24. In some embodiments, the distal end 22 of the blood collection device 20 may include a male luer adapter 26, which may include a distal opening 28. In some embodiments, the blood collection device 20 may include a cannula 30 in fluid communication with the male luer adapter 26. In some embodiments, the cannula 30 may include a distal end 32 and a sharp proximal tip 34. In some embodiments, the cannula 30 may be constructed of metal or another suitable material configured to punctuate a seal of a blood collection container, such as a blood collection tube. In some embodiments, an elastomeric sheath 31, and in response to insertion of the blood collection container being inserted into the blood collection device 20, the sharp proximal tip 34 may puncture the elastomeric sheath 31, which may be compressed in a distal direction by the blood collection container.

In some embodiments, the blood collection device 20 may include an elongated neck 35 disposed between the male luer adapter 26 and the sharp proximal tip 34. In some embodiments, the blood collection device 20 may include a fluid pathway 36 extending from the distal opening 28 through the sharp proximal tip 34. In some embodiments, a diameter 37 of the fluid pathway 36 is constant. In some embodiments, an entire length 38 of the fluid pathway 36 is represented by L, and the diameter 37 of the fluid pathway 36 is represented by D, as will be referred to later in further detail.

In some embodiments, the male luer adapter 26 of the blood collection device 20 may include a collar 39, which may extend around a protrusion 40 of the male luer adapter 26. In some embodiments, the distal opening 28 may be disposed within a distal-most portion of the protrusion 40. In some embodiments, an inner surface of the collar 39 may be threaded to form a luer-lock fit with a corresponding female luer adapter. In other embodiments, the inner surface of the collar 39 may be smooth to form a slip-fit with a corresponding female luer adapter. In some embodiments, the fluid pathway 36 may be formed entirely by the cannula 30, which may extend through the collar 39 and form the protrusion 40 and the distal opening 28.

In some embodiments, an outer diameter of the collar 39 may be greater than an outer diameter of the elongated neck 35. In some embodiments, the blood collection device 20 may include a holder 41 configured to receive a blood collection container, such as a blood collection tube. In some embodiments, the holder 41 may include a cylindrical body 42. In some embodiments, the sharp proximal tip 34 may be disposed in a center of the cylindrical body 42 to facilitate puncture of a seal of the blood collection container in response to insertion of the blood collection container within a proximal opening 44 of the cylindrical body 42.

In some embodiments, an outer diameter of the cylindrical body 42 may be greater than the outer diameter of the elongated neck 35. In some embodiments, the elongated neck 35 may be disposed between the holder 41 and the collar 39. In some embodiments, the distal end 32 of the cannula 30 may be integrated and secured within the elongated neck 35. In some embodiments, the elastomeric sheath 21 may be coupled to an inner surface of the holder 41.

Figure 2C:
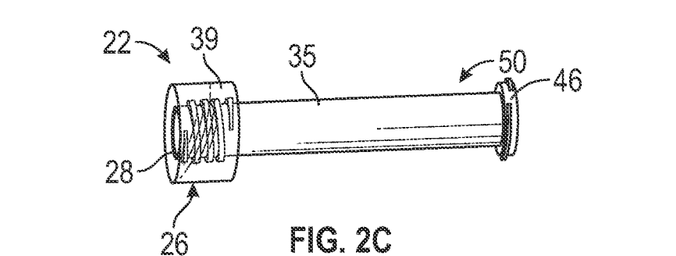
FIG. 2C is an upper perspective view of an example portion of the blood collection device, according to some embodiments.
Figure 2D:
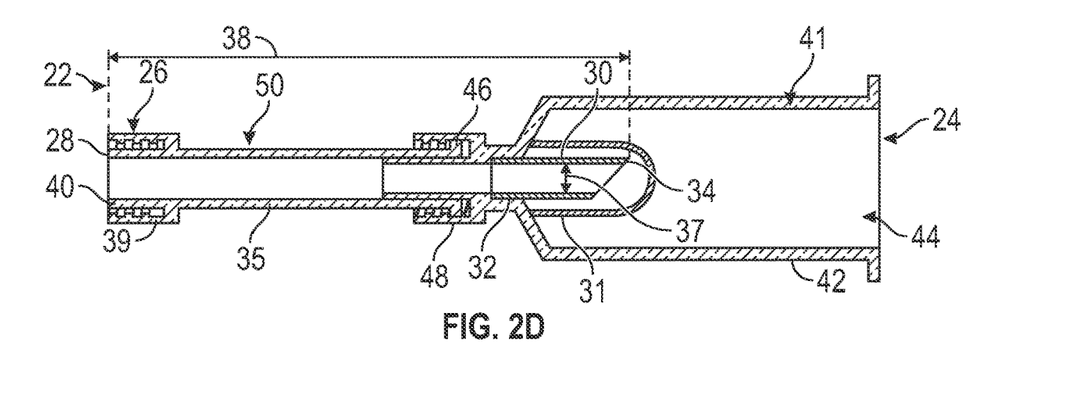
FIG. 2D is a cross-sectional view of the portion coupled to a remaining portion of the blood collection device, according to some embodiments.

Referring now to FIGS. 2C-2D, in some embodiments, the blood collection device 20 may include a female luer adapter 46 disposed at a proximal end of the elongated neck 35. In some embodiments, the distal end of the holder 41 may include a male luer adapter 48. In some embodiments, the female luer adapter 46 may be coupled to the male luer adapter 48. Thus, in some embodiments, the blood collection device 20 may include an extension 50, which a user may couple to the holder 41 to provide the elongated neck 35 and an increased L, which may decrease the risk of hemolysis. In these and other embodiments, D may correspond to an inner diameter of the cannula 30. In some embodiments, an inner diameter of the elongated neck 35 may be equal to D along all or a portion of the elongated neck 35. In some embodiments, the male luer adapter 48 may be similar or identical to the male luer adapter 26 in terms of one or more features and/or operation.

Figure 3A:
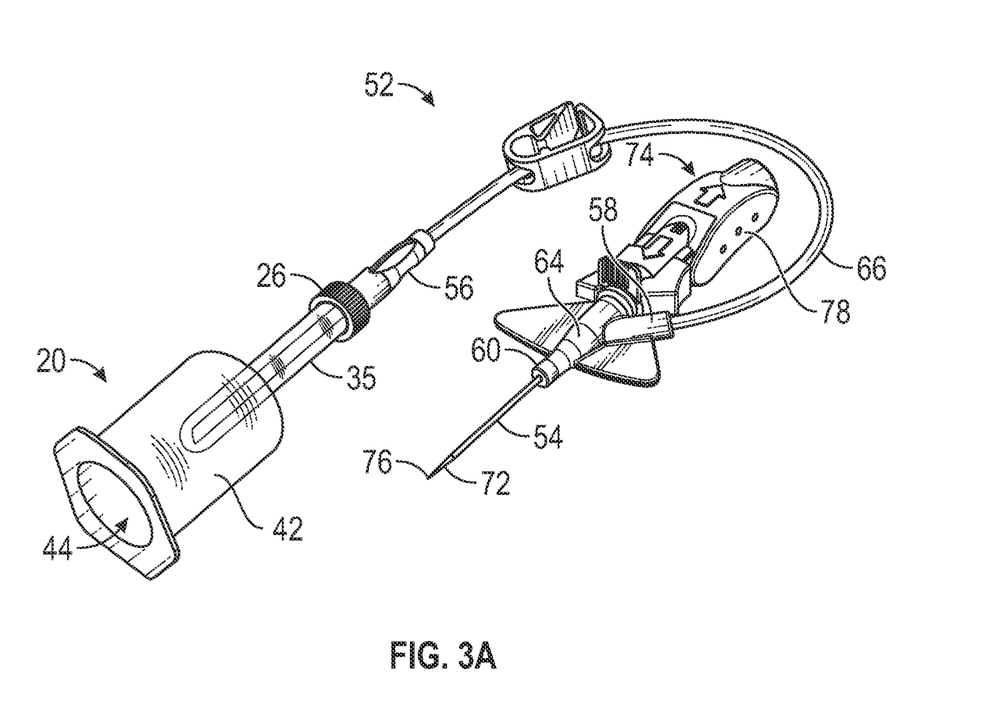
FIG. 3A is an upper perspective view of an example peripheral intravenous catheter system, according to some embodiments.
Figure 3B:
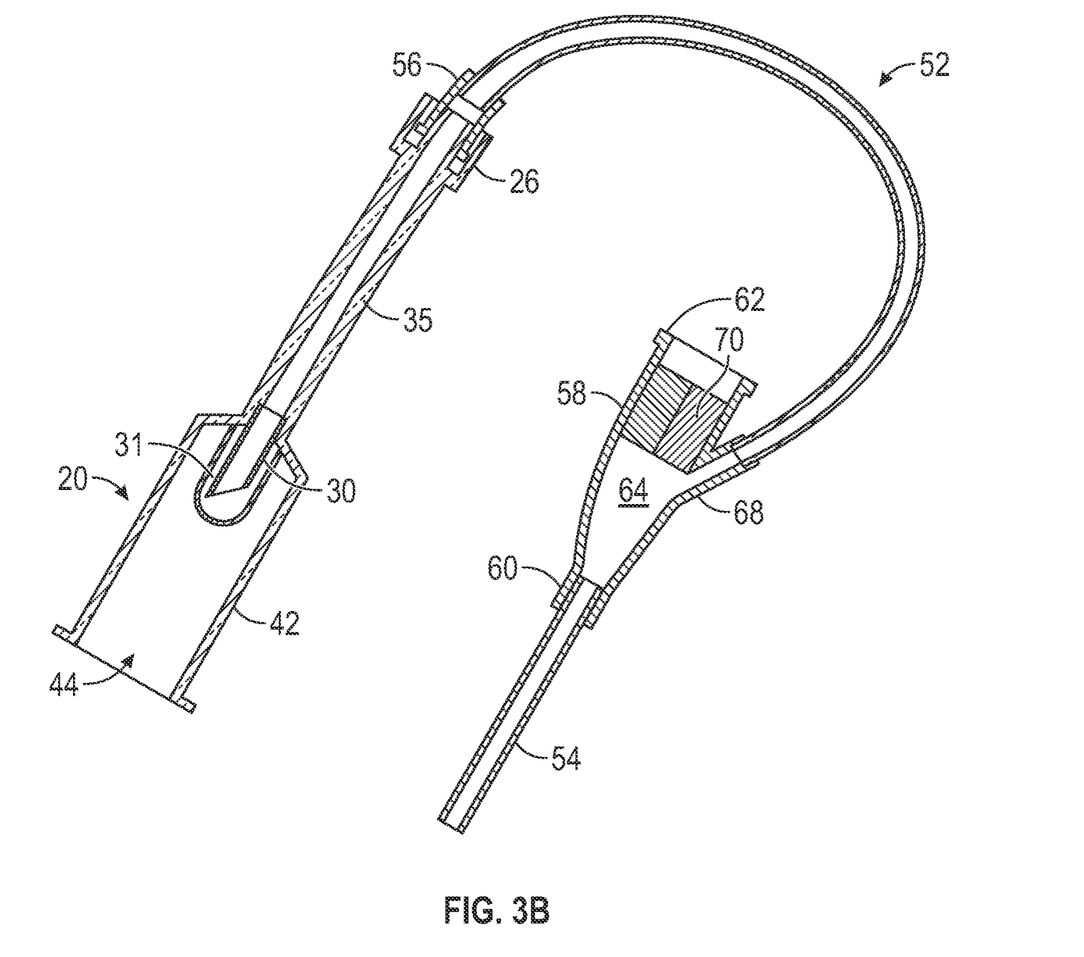
FIG. 3B is a cross-sectional view of the peripheral intravenous catheter system, illustrating an example needle assembly removed, according to some embodiments.

Referring now to FIGS. 3A-3B, a peripheral intravenous catheter system 52 is illustrated, according to some embodiments. In some embodiments, the peripheral intravenous catheter system 52 may include a peripheral intravenous catheter 54, and a female luer adapter 56 coupled to the peripheral intravenous catheter 54. In some embodiments, the peripheral intravenous catheter system 52 may include the blood collection device 20, which may reduce the risk of hemolysis.

In some embodiments, the peripheral intravenous catheter system 52 may include a catheter adapter 58, which may include a distal end 60, a proximal end 62, and a lumen 64 extending through the distal end 60 of the catheter adapter 58 and the proximal end 62 of the catheter adapter 58. In some embodiments, the peripheral intravenous catheter 54 may extend distally from the distal end 60 of the catheter adapter 58.

In some embodiments, the male luer adapter 26 of the blood collection device 20 may be coupled to the female luer adapter 56. In some embodiments, the peripheral intravenous catheter system 52 and/or a location of the female luer adapter 56 may vary. In some embodiments, the peripheral intravenous catheter system 52 may include an extension tube 66, which may include a distal end integrated with a side port 68 of the catheter adapter 58 and a proximal end integrated with the female luer adapter 56. In some embodiments, the side port 68 may be disposed in between the distal end 60 and the proximal end 62 of the catheter adapter 58 and in fluid communication with the lumen 64. In some embodiments, the proximal end 62 of the catheter adapter 58 may include the female luer adapter 56, and the blood collection device 20 may be coupled to the proximal end 62 of the catheter adapter 58.

In some embodiments, a septum 70 may be disposed within the lumen 64 of the catheter adapter 58. In some embodiments, an introducer needle 72 of a needle assembly 74 may extend through the septum 70 and the peripheral intravenous catheter 54 when the peripheral intravenous catheter system 52 is inserted into the vasculature of the patient. In some embodiments, the needle assembly 74 may be removed from the peripheral intravenous catheter system 52 in response to the peripheral intravenous catheter 54 being inserted into the vasculature. In some embodiments, the introducer needle 72 may include a sharp distal tip 76 and may extend from a needle hub 78 of the needle assembly 74, which may be coupled to the proximal end 62 of the catheter adapter 58.

Typically, a maximum shear stress during blood collection through a peripheral intravenous catheter 54 is much higher than a maximum shear stress during blood collection using another type of catheter. In some embodiments, the entire length of the fluid pathway 36 is between 2 inches and 5.4 inches, inclusive, which may reduce maximum shear stress during blood collection. In some embodiments, a gauge of the peripheral intravenous catheter 54 is between 22 G and 18 G, inclusive, and the entire length of the fluid pathway 36 may be approximately 2 inches. In some embodiments, increasing the entire length of the fluid pathway 36 from 1 inch (as in the prior art blood collection device 10 of FIGS. 1A-1B) to approximately 2 inches for the peripheral intravenous catheter 54 that is 22 G-18 G (inclusive) decreased the maximum shear stress during blood collection an unexpected amount.

In some embodiments, the gauge of the peripheral intravenous catheter is 24 G, and the entire length of the fluid pathway 36 may be approximately 5.4 inches. In some embodiments, increasing the entire length of the fluid pathway 36 from 1 inch (as in the prior art blood collection device 10 of FIGS. 1A-1B) to approximately 5.4 inches for the peripheral intravenous catheter 54 that is 24 G decreased the maximum shear stress during blood collection an unexpected amount.

In some embodiments, the diameter of the fluid pathway 36 may be greater than a minimum inner diameter of the peripheral intravenous catheter 54. In some embodiments, $D^4/L$ is equal to or less than a predetermined value, which may be based on the gauge of the peripheral intravenous catheter 54. In some embodiments, the predetermined value may correspond to a value at which the risk of hemolysis is determined to be low. In some embodiments, the gauge of the peripheral intravenous catheter is 24 G, and $D^4/L$ is equal to or less than 5.8E-08 cubic inches. In some embodiments, the gauge of the peripheral intravenous catheter is 22 G, and $D^4/L$ is equal to or less than 1.6E-07 cubic inches. In some embodiments, the gauge of the peripheral intravenous catheter is 20 G, and $D^4/L$ is equal to or less than 3.1E-07 cubic inches. In some embodiments, the gauge of the peripheral intravenous catheter is 18 G, and $D^4/L$ is equal to or less than 5.8E-08 cubic inches.

Figure 4A:
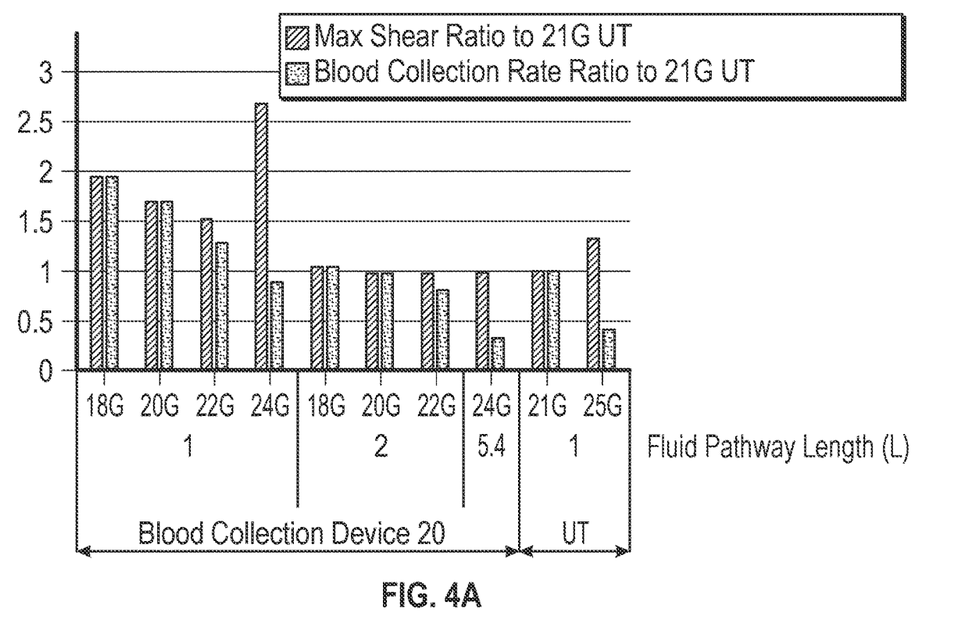
FIG. 4A is a bar graph illustrating an average of max shear ratio and an average of blood collection rate ratio for example blood collection devices compared to a best-in-class prior art blood collection device, where each of the blood collection devices includes a fluid pathway having the entire length represented by L, according to some embodiments.

Referring now to FIG. 4A, a bar graph illustrates a maximum shear ratio and a blood collection rate ratio for the blood collection device 20 compared to a best-in-class prior art blood collection device, namely the 21 G BD VACUTAINER® ULTRATOUCH™ push button blood collection set (referred to as "21 G UT w BC Set" or "UT"). In some embodiments, the gauge of the peripheral intravenous catheter is 24 G, and the entire length of the fluid pathway 36 may be approximately 5.4 inches. In some embodiments, increasing the entire length of the fluid pathway 36 from 1 inch (as in the prior art blood collection device 10 of FIGS. 1A-1B) to approximately 5.4 inches for the peripheral intravenous catheter 54 that is 24 G decreased the maximum shear stress ratio to UT during blood collection an unexpected amount. In some embodiments, increasing the entire length of the fluid pathway 36 (see FIG. 2) from 1 inch (as in the prior art blood collection device 10 of FIGS. 1A-1B) to approximately 2 inches with the peripheral intravenous catheter 54 (see FIG. 3) that is 18 G-22 G decreased the maximum shear stress ratio to UT during blood collection an unexpected amount.

Figure 4B:
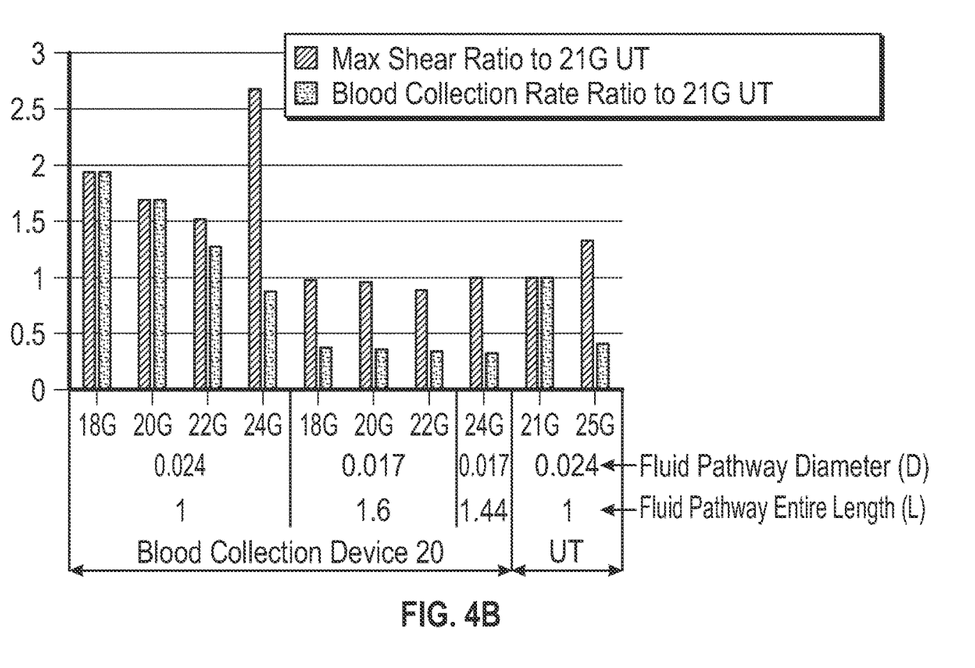
FIG. 4B is a bar graph illustrating a sum of max shear ratio and a sum of blood collection rate ratio for example blood collection devices compared to the best-in-class prior art blood collection device, where each of the blood collection devices includes the fluid pathway having an entire length represented by L, according to some embodiments.

In some embodiments, with the peripheral intravenous catheter 54 that is 18 G or 20 G, a blood collection rate will be the same as the UT once the maximum shear stresses are matched. In some embodiments, with the peripheral intravenous catheter 54 that is 22 G, the blood collection rate may be slightly slower than that of UT, while for the peripheral intravenous catheter 54 that is 24 G, the blood collection rate is significantly lower than that of UT when the maximum shear is matched. Referring now to FIG. 4B, a bar graph illustrates a maximum shear ratio and a blood collection rate ratio for the blood collection device 20 compared to a best-in-class prior art blood collection device, namely the 21 G BD VACUTAINER® ULTRATOUCH™ push button blood collection set (referred to as "21 G UT w BC Set" or "UT"). Results for the blood collection device 20 having D equal to 0.024 inches and 0.017 inches are illustrated. Results for the blood collection device 20 having L equal to 1 inch, 1.6 inches, and 1.44 inches are illustrated.

In some embodiments, with the peripheral intravenous catheter 54 that is 24 G, L of the fluid pathway 36 can be reduced significantly to 1.44 inches if D of the fluid pathway 36 is reduced to 0.017 inches, which may be just larger than a minimum inner diameter of a tip of the peripheral intravenous catheter 54. In some embodiments, as long as D is greater than the minimum inner diameter of the tip and $D^4/L$ is kept at 5.8e-8 cubic inches, the maximum shear stress in blood draw with the peripheral intravenous catheter 54 that is 24 G will match that of UT. Similarly, in some embodiments, with the peripheral intravenous catheter 54 that is 22 G-18 G (inclusive), L of the fluid pathway 36 can be reduced significantly to 1.6 inches in order to match the max shear stress of UT. However, in some embodiments, a blood draw rate is only ⅓ of UT as illustrated in FIG. 4B.

Figure 4C:
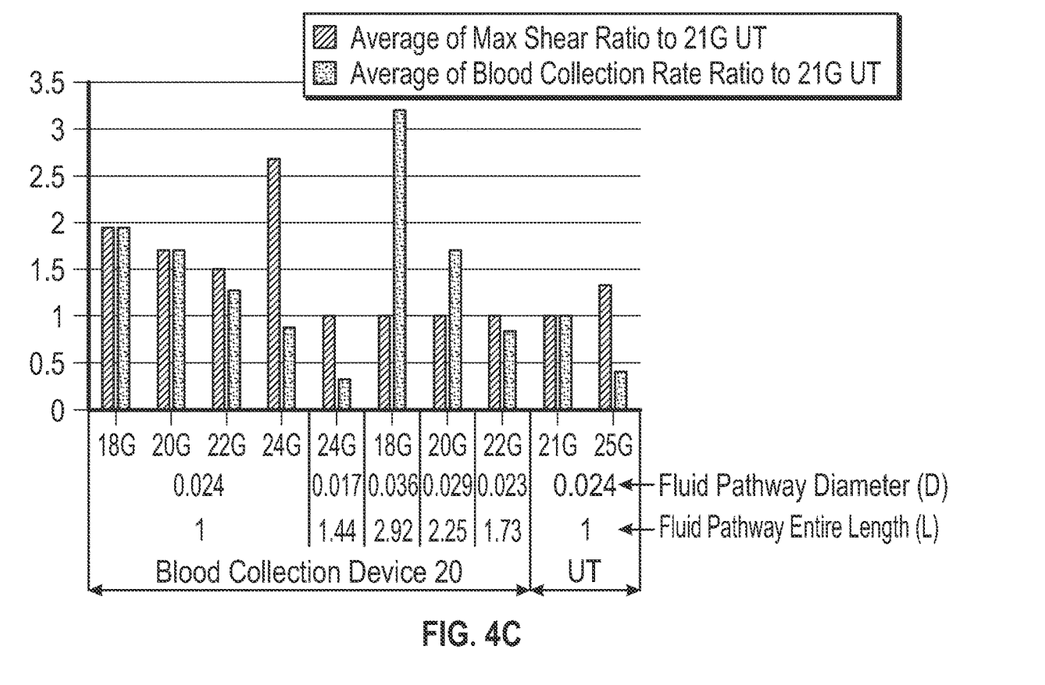
FIG. 4C is a bar graph illustrating an average max shear ratio and an average blood collection rate ratio for example blood collection devices compared to the best-in-class prior art blood collection device, where each of the blood collection devices includes the fluid pathway having the entire length represented by L, according to some embodiments.

Referring now to FIG. 4C, a bar graph illustrates a maximum shear ratio and a blood collection rate ratio for the blood collection device 20 compared to the best-in-class prior art blood collection device, namely the 21 G BD VACUTAINER® ULTRATOUCH™ push button blood collection set (referred to as "21 G UT w BC Set" or "UT"). Results for the blood collection device 20 having D equal to 0.024 inches, 0.017 inches, 0.036 inches, 0.029 inches, and 0.023 inches are illustrated. Results for the blood collection device 20 having L equal to 1 inch, 1.44 inches, 2.92 inches, 2.25 inches, and 1.73 inches are illustrated. In some embodiments, different geometries of the blood collection device 20 may be used for different catheter gauges.

In some embodiments, the limiting factor in blood collection rate when matching the max shear stress to UT is a smallest inner diameter in the peripheral intravenous catheter system, which may be the minimum inner diameter of the tip of the peripheral intravenous catheter 54. For the peripheral intravenous catheter 54 that is 20 G or 18 G, the blood collection rate can be increased by increasing D of the fluid pathway 36. In some embodiments, the blood collection rate can be increased by increasing D to be greater than the smallest inner diameter in the peripheral intravenous catheter system. In some embodiments, the maximum shear stress can be lowered to match or be less than that of UT by increasing L while maintaining $D^4/L$ less than a predetermined or critical value. In some embodiments, with the peripheral intravenous catheter 54 that is 22 G, by reducing D to be just larger than the minimum inner diameter of the tip, L can be reduced to 1.73 inches from 2 inches when matching the max shear of UT.

In some embodiments, a method of manufacturing the peripheral intravenous catheter system may include selecting a target maximum shear stress, such as that of UT. In some embodiments, the method may include reducing a current maximum shear stress of the peripheral intravenous catheter system by increasing L while maintaining $D^4/L$ to be equal to or less than the predetermined value.

All examples and conditional language recited herein are intended for pedagogical objects to aid the reader in understanding the present disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

We claim:

1. A peripheral intravenous catheter system to reduce a risk of hemolysis, comprising:
    a peripheral intravenous catheter;
    a female luer adapter coupled to the peripheral intravenous catheter;
    a blood collection device, comprising:
    a distal end, comprising a male luer adapter coupled to the female luer adapter, the male luer adapter comprising a distal opening;
    a cannula in fluid communication with the male luer adapter, wherein the cannula comprises a distal end and a sharp proximal tip;
    an elongated neck disposed between the male luer adapter and the sharp proximal tip; and
    a fluid pathway extending from the distal opening through the sharp proximal tip, wherein a diameter of the fluid pathway is constant and greater than a minimum inner diameter of the peripheral intravenous catheter, such that the fluid pathway is configured to increase flow rate and decrease shear stress, wherein an entire length of the fluid pathway is represented by L, wherein the diameter of the fluid pathway is represented by D, and wherein the peripheral intravenous catheter is at least one of:
        (i) a 20 gauge (G) catheter, wherein $D^4/L$ is equal to or less than 3.1E-07 cubic inches; and
        (ii) an 18 gauge (G) catheter, wherein $D^4/L$ is equal to or less than 5.8E-08 cubic inches.

2. The catheter system of claim 1, wherein the entire length of the fluid pathway is 2 inches.

3. The catheter system of claim 1, wherein a gauge of the peripheral intravenous catheter is 20 gauge (G) and $D^4/L$ is equal to or less than 3.1E-07 cubic inches.

4. The catheter system of claim 1, wherein a gauge of the peripheral intravenous catheter is 18 gauge (G) and $D^4/L$ is equal to or less than 5.8E-08 cubic inches.

5. The catheter system of claim 1, wherein the male luer adapter comprises a collar, wherein an outer diameter of the collar is greater than an outer diameter of the elongated neck.

6. The catheter system of claim 5, wherein the blood collection device further comprises a holder configured to receive a blood collection tube, wherein the holder comprises a cylindrical body, wherein the sharp proximal tip is disposed in a center of the cylindrical body.

7. The catheter system of claim 6, wherein an outer diameter of the holder is greater than the outer diameter of the elongated neck, wherein the elongated neck is disposed between the holder and the collar.

8. The catheter system of claim 1, wherein the distal end of the cannula is integrated within the elongated neck.

9. The catheter system of claim 6, wherein the blood collection device further comprises another female luer adapter disposed at a proximal end of the elongated neck, wherein a distal end of the holder comprises another male luer adapter, wherein the other female luer adapter is coupled to the other male luer adapter.

10. A blood collection device to reduce a risk of hemolysis in a peripheral intravenous catheter system, the blood collection device comprising:
- a distal end comprising a male luer adapter, wherein the male luer adapter comprises a distal opening;
- a cannula in fluid communication with the male luer adapter, wherein the cannula comprises a distal end and a sharp proximal tip;
- an elongated neck disposed between the male luer adapter and the sharp proximal tip; and
- a fluid pathway extending from the distal opening through the sharp proximal tip, wherein a diameter of the fluid pathway is constant, wherein an entire length of the fluid pathway is represented by L, wherein the diameter of the fluid pathway is represented by D, and wherein the blood collection device is gauge specific and configured for use with at least one of:
  (i) a 20 gauge (G) catheter, wherein $D^4/L$ is equal to or less than 3.1E-07 cubic inches; and
  (ii) an 18 gauge (G) catheter, wherein $D^4/L$ is equal to or less than 5.8E-08 cubic inches,
  to create a fluid pathway configured to increase flow rate and decrease shear stress.

11. The blood collection device of claim 10, wherein the entire length of the fluid pathway is between 2 inches and 5.4 inches, inclusive.

12. The blood collection device of claim 10, wherein D is greater than or equal to an inner diameter of the catheter.

13. The blood collection device of claim 12, wherein the blood collection device further comprises a holder configured to receive a blood collection tube, wherein the holder comprises a cylindrical body, wherein the sharp proximal tip is disposed in a center of the cylindrical body.

14. The blood collection device of claim 13, wherein an outer diameter of the holder is greater than an outer diameter of the elongated neck.

15. The blood collection device of claim 13, wherein the distal end of the cannula is integrated within the elongated neck.

16. The blood collection device of claim 13, wherein the blood collection device further comprises another female luer adapter disposed at a proximal end of the elongated neck, wherein the distal end of the holder comprises another male luer adapter, wherein the other female luer adapter is coupled to the other male luer adapter.

* * * * *